United States Patent [19]

Funakoshi

[11] Patent Number: 5,111,804
[45] Date of Patent: May 12, 1992

[54] ELECTRONIC ENDOSCOPE

[75] Inventor: Toshio Funakoshi, Tochigi, Japan

[73] Assignee: Kabushiki Kaisha Toshiba, Kawasaki, Japan

[21] Appl. No.: 479,411

[22] Filed: Feb. 13, 1990

[30] Foreign Application Priority Data

Feb. 15, 1989 [JP] Japan .................... 1-033812

[51] Int. Cl.$^5$ .................. A61B 1/04; H04N 11/00
[52] U.S. Cl. .................... 128/6; 358/98
[58] Field of Search ............ 128/4, 6; 358/98

[56] References Cited

U.S. PATENT DOCUMENTS

| | | | |
|---|---|---|---|
| 4,562,831 | 1/1986 | Murakoshi et al. | 128/6 |
| 4,766,489 | 8/1988 | Kato | 358/98 |
| 4,799,104 | 1/1989 | Hosoya et al. | 358/98 |
| 4,819,077 | 4/1989 | Kikuchi et al. | 358/98 |
| 4,831,437 | 5/1989 | Nishioka et al. | 358/98 |
| 4,891,696 | 1/1990 | Miyazaki et al. | 128/6 |
| 5,007,407 | 4/1991 | Kikuchi | 128/6 |

Primary Examiner—Stephen C. Pellegrino
Assistant Examiner—Ralph A. Lewis
Attorney, Agent, or Firm—Foley & Lardner

[57] ABSTRACT

An electronic endoscope including a scope having an image pickup device, such as a CCD, for picking up color image signls of an object to be observed, and a light source unit for outputting to the scope either a continuous DC light in a moving image pickup operation or a pulsed light in a still image pickup operation for illuminating the object. A color separation circuit calculates white balance factors for primary colors, a multiplier calculates color correction factors for the primary colors, a multiplier carries out a white balance operation of the color image signals by multiplying the white balance factors thereto, and an image memory carries out a color correction operation of the color image signals by multiplying the color correction factors thereto in the still image pickup operation.

17 Claims, 3 Drawing Sheets

ELECTRONIC ENDOSCOPE

BACKGROUND OF THE INVENTION

1. Field of the Invention

The present invention relates to an electronic endoscope, and more particularly to an improvement of a white balance adjustment in an electronic endoscope when a color still image is picked up.

2. Description of the Background Art

In a conventional endoscope, when a moving image pickup operation is carried out, continuous lighting of a light source is achieved by applying a DC current, and, in turn, when a still image pickup operation is carried out in response to a freezing command, a pulsed lighting is used by applying a modulated pulse signal. In this case, even when a change between the moving and still image pickup operations is conducted, there is no difference in brightness to obtain a clear color image on a display without incurring blur in the still image pickup operation.

Since the inside of internal organs such as stomach or the like is reddish, when it is observed by using an endoscope without having a color adjustment of picture image signals in consideration of such a reddish color, the whole of the obtained color image becomes reddish. In the conventional endoscope, in order to prevent this problem, a so-called white balance adjustment is carried out. That is, factors for making the intensity of the picture image signals for three primary colors such as red (R), green (G) and blue (B) equal when the picture image signals are picked up by imaging a standard white color plate, are obtained and multiplied to the picture image signals for the primary colors.

However, spectral characteristics such as intensity of an emitted light of a xenon lamp usually used as a light source is different between the continuous DC current lighting in the moving image pickup operation and the pulsed lighting in the still image pickup operation, as shown by a solid line A (continuous DC light) and a broken line B (pulsed light) in FIG. 5. Hence, when the operation is changed from the moving image pickup to the still image pickup, the color tone of the obtained image is changed. That is, in a conventional endoscope of this kind, the white balance adjustment is carried out without taking consideration of the intensity difference of the emitted light of the xenon lamp between the DC lighting and the pulsed lighting, and hence, when the operation is changed from the moving image pickup to the still image pickup, the color tone of the reproduced color picture image is changed. This makes it difficult for an operator to observe the inside of an internal organ and diagnosis a patient.

SUMMARY OF THE INVENTION

Accordingly, it is an object of the present invention to provide an electronic endoscope, free from the aforementioned defects and disadvantages of the prior art, which is capable of performing a white balance adjustment of color image signals without changing a color tone of a color picture image when an operation is changed from a moving image pickup to a still image pickup.

In accordance with one aspect of the present invention, there is provided an endoscope, comprising a scope having an image pickup device for picking up color image signals of an object to be observed, a light source unit for outputting either a continuous DC light in a moving image pickup operation or a pulsed light in a still image pickup operation to the scope for illuminating the object, first means for obtaining white balance factors for primary colors, second means for obtaining color correction factors for the primary colors, third means for carrying out a white balance operation of the color image signals by multiplying the white balance factors thereto, and fourth means for carrying out a color correction operation of the color image signals by multiplying the color correction factors thereto in the still image pickup operation.

In accordance with another aspect of the present invention, there is provided an endoscope, comprising a scope having an image pickup device for picking up color image signals of an object to be observed, a light source unit for outputting either a continuous DC light in a moving image pickup operation or a pulsed light in a still image pickup operation to the scope for illuminating the object, first means for obtaining white balance factors for primary colors, third means for carrying out a white balance operation of the color image signals by multiplying the white balance factors thereto, and filter means having approximately the same wave length property as that of the continuous DC light in a lower half wave length band thereof for carrying out a color correction operation of the color image signals in the still image pickup operation, the filter means being to be inserted in a path of the pulsed light emitted by the light source unit in the still image pickup operation.

BRIEF DESCRIPTION OF THE DRAWINGS

The above and other objects, features and advantages of the present invention will more fully appear from the following description of the preferred embodiments with reference to the accompanying drawings, in which.

DESCRIPTION OF THE PREFERRED EMBODIMENTS

Figure 1:
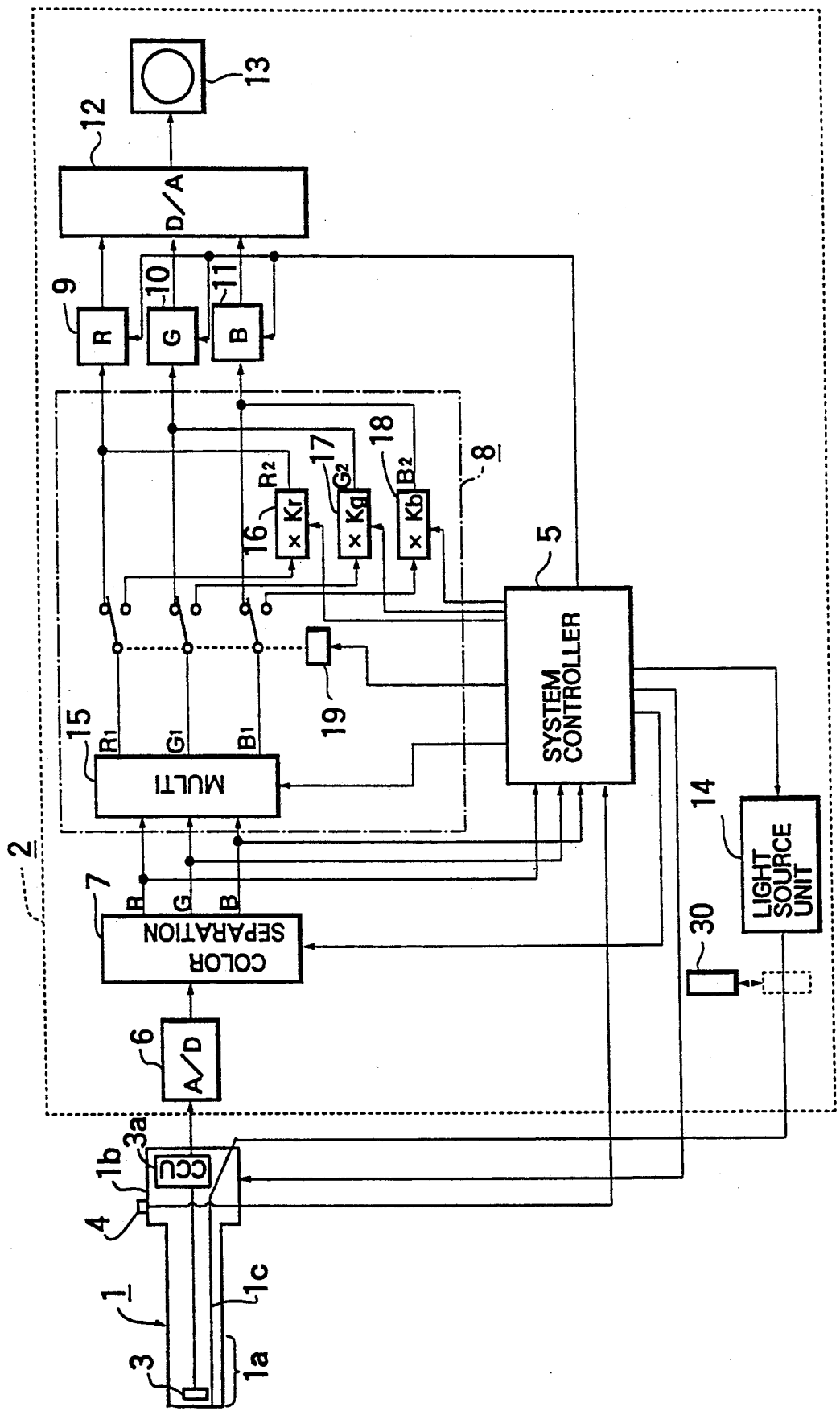
FIG. 1 is a block diagram of a first embodiment of an electronic endoscope according to the present invention.

Referring now to the drawings, wherein like reference characters designate like or corresponding components throughout the several views and, thus, a repeated description can be omitted, there is shown in FIG. 1 the first embodiment of an electronic endoscope according to the present invention.

In FIG. 1, the endoscope comprises a scope 1 and a body 2. The scope 1 includes a solid-state image pickup device such as CCD (charge coupled devices) 3 in a tip portion 1a, a CCU (camera control unit) 3a connected to the CCD 3 and a freeze switch 4 in an operational portion 1b. The scope 1 also includes a light guide 1c to be connected to a light source unit 14. In this case, three kinds of filter pieces (not shown) for three primary colors such as red (R), green (G) and blue (B) are attached to the incident surface of the CCD 3 in the predetermined alignment, and hence color image information of the three primary colors for reproducing a color image can be obtained in a single image pickup operation.

In the body 2, a system controller 5 controls the entire system of the endoscope, and an A/D (analog-digital) converter 6 receives analog color image signals output from the CCU 3a in the scope 1 and outputs digital color image signals to a color separation circuit 7. The color separation circuit 7 performs a color separation of the digital color image signals and outputs color-separated color image signals R, G, B to a white balance circuit 8 for carrying out a white balance adjustment of moving and still color image signals, as hereinafter described in detail. Three image memories 9, 10 and 11 store the white-balanced color image signals for the three primary colors, output from the white balance circuit 8. The color image signals read out of the three image memories 9, 10 and 11 are fed to a D/A (digital-analog) converter 12 which outputs analog color image signals to a color display 13. The color display 13 displays a reproduction color image thereon. A light source unit 14 is provided with a xenon lamp which is controlled so as to emit a continuous DC light in a moving image pickup and a modulated pulsed light in a still image pickup. The illumination light emitted by the light source unit 14 is sent to the scope 1 through the light guide 1c.

The white balance circuit 8 includes a multiplier 15 for setting white balance factors Wf, and Wg and Wb therein, another three multipliers 16, 17 and 18 for setting color correction factors Kr, Kg and Kb, respectively, therein and a triple switch assembly 19. The multiplier 15 receives the digital color image signals R, G and B for the three primary colors from the color separation circuit 7 and multiplies the white balance factors Wf, Wg and Wb to the respective digital color image signals R, G and B to output white-balanced digital color image signals $R_1$, $G_1$ and $B_1$ to the triple switch assembly 19. The triple switch assembly 19 switches so as to selectively send the digital color image signals $R_1$, $G_1$ and $B_1$ to the respective three image memories 9, 10 and 11 in the moving image pickup operation or to the respective three multipliers 16, 17 and 18 in the still image pickup operation. The three multipliers 16, 17 and 18 multiply the color correction factors Kr, Kg and Kb for the three primary colors to the respective color image signals $R_1$, $G_1$ and $B_1$ to output color-corrected color image signals $R_2$, $G_2$ and $B_2$ to the respective three image memories 9, 10 and 11 in the still image pickup operation.

In this embodiment, in the system controller 5, the white balance factors Wr, Wg and Wb for the three primary colors and the color correction factors Kr, Kg and Kb for the three primary colors are calculated in a conventional manner. That is, in the moving image pickup operation, the color image signals R, G and B are obtained by imaging a reference or standard white color plate, and the white balance factors Wr, Wg and Wb for equalizing the intensity of the respective color image signals R, G and B to obtain the respective white-balanced color image signals $R_1$, $G_1$ and $B_1$ are so determined that $R \cdot Wr = R_1$, $G \cdot Wg = G_1$ and $B \cdot Wb = B_1$ and that the intensity of the white-balanced color image signals $R_1$, $G_1$ and $B_1$ is equal. The obtained white balance factors Wr, Wg and Wb for the three primary colors are set in the multiplier 15 in the white balance circuit 8 for carrying out the white balance operation.

Then, in the still image pickup operation, the color image signals R, G and B are obtained by imaging a standard white color plate, and the color correction factors Kr, Kg and Kb for equilizing the intensity of the respective color image signals $R_1$, $G_1$ and $B_1$ to obtain the respective colorcorrected color image signals $R_2$, $G_2$ and $B_2$ are so determined that $R_1 \cdot Kr = R_2$, $G_1 \cdot Kg = G_2$ and $B_1 \cdot Kb = B_2$ and that the intensity of the color-corrected color image signals $R_2$, $G_2$ and $B_2$ is equal. The obtained color correction factors Kr, Kg and Kb for the three primary colors are set in the respective multipliers 16, 17 and 18 in the white balance circuit 8 for carrying out the color correction operation. According to the present invention, the white balance adjustment includes the above described white-balance operation and the color-correction operation.

In this embodiment, when the freeze switch is pushed on during the moving image pickup operation, a freeze command signal is sent from the system controller 5 to the related members, and then the members such as the light source unit 14, the triple switch assembly 19 and the image memories 9, 10 and 11 are changed from the moving image pickup mode to the still image pickup mode.

The operation of the above described endoscope will be described as follows.

In the moving image pickup operation, as described above, the inside of the organ is illuminated by the continuous DC light sent from the light source unit 14 to the tip portion 1a of the scope 1 through the light guide 1c, and the light reflected by the inside wall of the internal organ is picked up by the CCD 3 in the scope 1. The output analog image signals of the CCD 3 are fed to the body 2 through the CCU 3a in the scope 1.

In the body 2, the analog image signals are sent to the A/D converter 6 and are converted into the digital image signals therein. The digital image signals are then fed to the color separation circuit 7, which outputs the color-separated digital color image signals R, G and B for the three primary colors to the multiplier 15. In the multiplier 15, the digital color image signals R, G and B are multiplied by the respective white balance factors Wr, Wg and Wb to output the white-balanced digital color image signals $R_1$, $G_1$ and $B_1$. The digital color image signals $R_1$, $G_1$ and $B_1$ are sent to the respective image memories 9, 10 and 11 through the triple switch assembly 19 and are stored in the respective image memories 9, 10 and 11. The digital color image signals $R_1$, $G_1$ and $B_1$ read out of the respective memories 9, 10 and 11 are sent to the D/A converter 12. The control of the writing or reading of the the digital color image signals $R_1$, $G_1$ and $B_1$ into or out of the respective image memories 9, 10 and 11 is carried out by the system controller 5. The digital color image signals $R_1$, $G_1$ and $B_1$ are converted into the analog color image signals in the D/A converter 12, and the obtained analog color image signals are sent to the color display 13. The white-balanced color reproduction image is displayed on the color display 13.

Then, in the still image pickup operation which is started by pushing on the freeze switch 4 of the scope 1, as described above, the inside of the organ is illuminated by the pulsed light sent from the light source unit 14 in the same manner as described above. The analog image signals picked up by the CCD 3 are fed to the the color separation circuit 7 through the CCU 3a and the A/D converter 6 in the same manner as described above. The color separation circuit 7 outputs the color-separated digital color image signals R, G and B for the three primary colors to the multiplier 15, and the multiplier 15 output the white-balanced digital color image signals $R_1$, $G_1$ and $B_1$. The digital color image signals $R_1$, $G_1$ and $B_1$ are sent to the respective multipliers 16, 17 and 18 through the triple switch assembly 19. In the multipliers 16, 17 and 18, the digital color image signals $R_1$, $G_1$ and $B_1$ are multiplied by the respective color correction factors Kr, Kg and Kb to obtain the respective color-corrected color image signals $R_2$, $G_2$ and $B_2$, which are sent to the respective image memories 9, 10 and 11. The color image signals $R_2$, $G_2$ and $B_2$ read out of the image memories 9, 10 and 11 are sent to the color display 13 through the D/A converter 12 in the same manner as described above. The white-balanced and color-corrected color reproduction image is displayed on the color display 13.

As described above, by carrying out the white balance adjustment composed of the white-balance operation and the color-correction operation, the color reproduction image can be clearly displayed on the color display without changing the color tone when the operation is changed from the moving image pickup to the still image pickup and vice versa. Therefore, the stable color tone of the reproduction image can be obtained regardless of the moving and still image pickup operations, and it is very much effective and helpful for the operator to carry out the diagnosis or the like.

Figure 2:
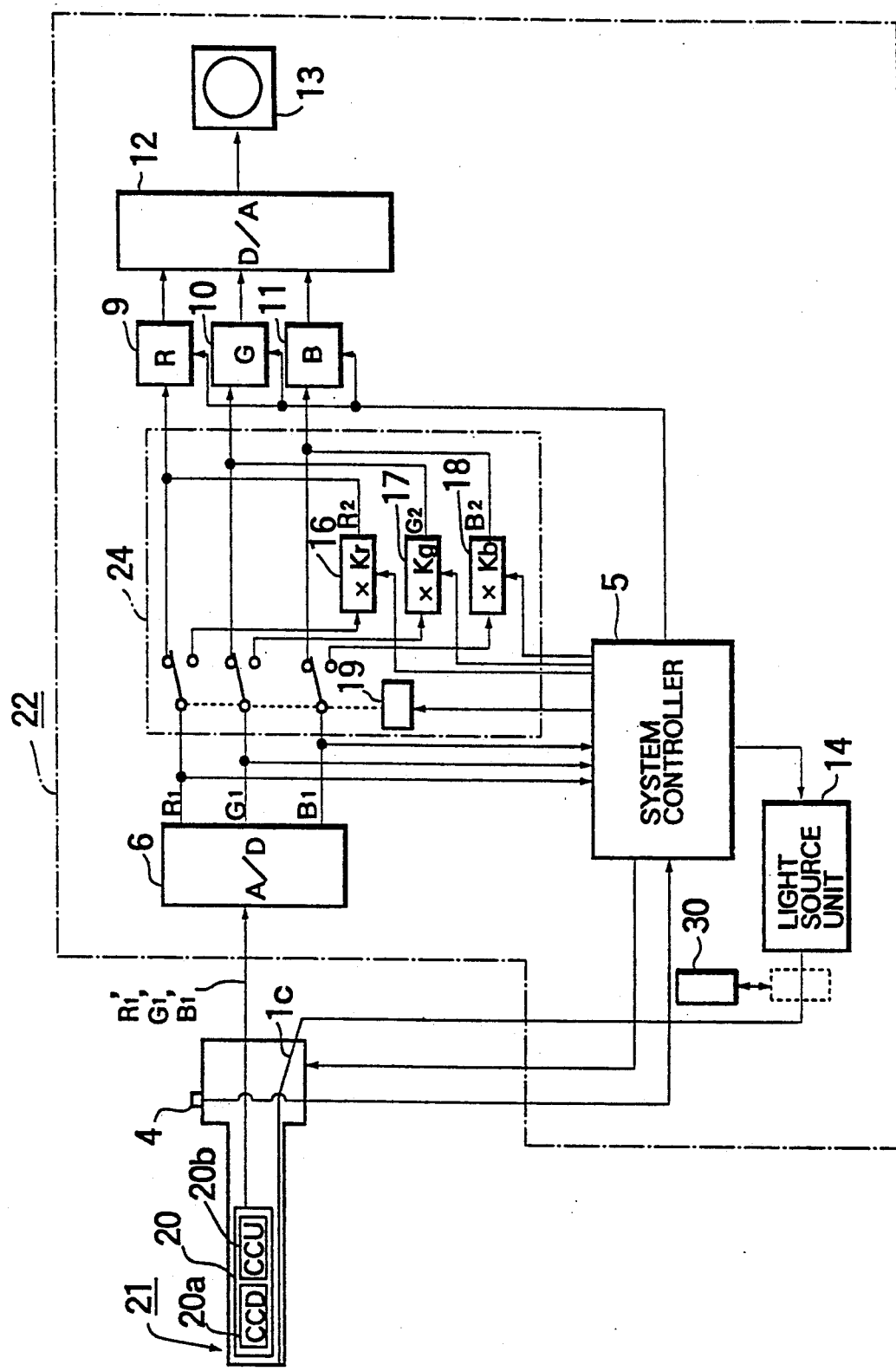
FIG. 2 is a block diagram of a second embodiment of an electronic endoscope according to the present invention.

In FIG. 2, there is shown the second embodiment of an electronic endoscope according to the present invention, having a similar construction to that of the first embodiment shown in FIG. 1. In this embodiment, the endoscope comprises a scope 21 and a body 22. The scope 21 is provided with a camera circuit 20 including a CCD 20a and a CCU 20b therein, and the white balance operation is carried out in the camera circuit 20 which outputs white-balanced analog color image signals $R_1'$, $G_1'$ and $B_1'$ to the body 22.

In this embodiment, the body 22 has the same structure as the body 2 in the first embodiment described above, except the multiplier 15 of the latter is omitted, and a white balance correction circuit 24 includes three multipliers 16, 17 and 18 and a triple switch assembly 19. The white-balanced analog color image signals $R_1'$, $G_1'$ and $B_1'$ output from the camera circuit 20 in the scope 21 are fed to an A/D converter 6, and the A/D converter 6 outputs the white-balanced digital color image signals $R_1$, $G_1$ and $B_1$. In system controller 5, only the color correction factors Kr, Kg and Kb for the three primary colors are calculated in the same manner as described above, and the color correction operation is carried out in the same manner as described above. In this embodiment, the same effects and advantages as those of the first embodiment can be obtained.

Figure 3:
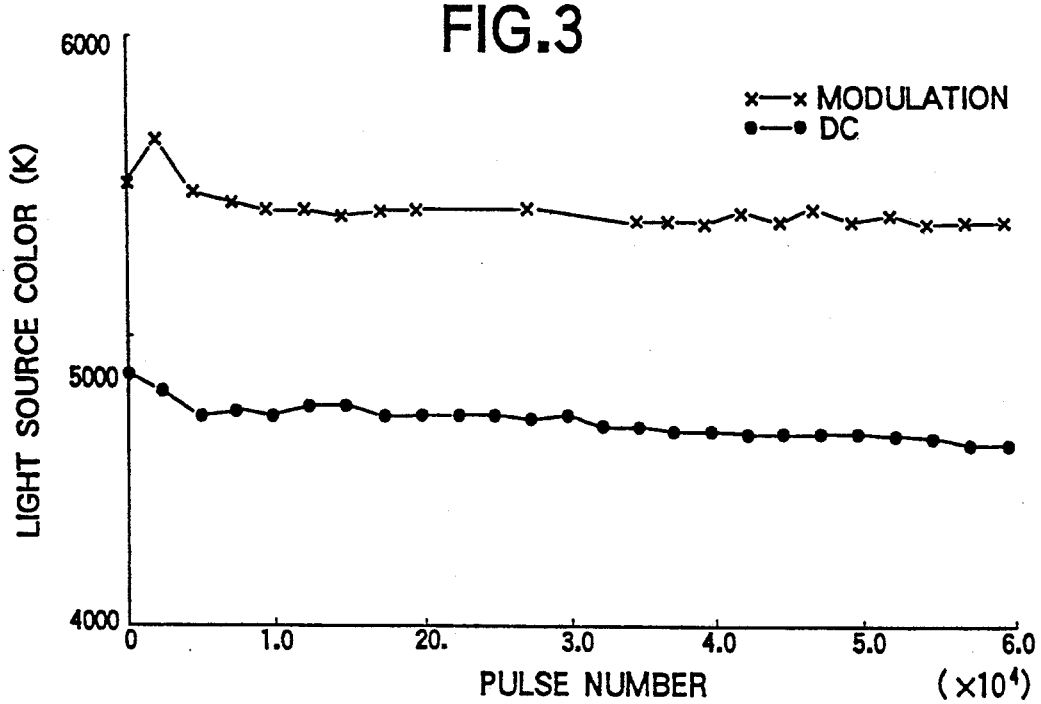
FIG. 3 is a graphical representation showing a pulse number property with respect to a light source color temperature for a DC light and a modulated pulsed light emitted by a xenon lamp of a light source used in the embodiments shown in FIGS. 1 and 2.

In FIG. 3, there is shown a pulse number property with respect to a light source color temperature for the DC light and the modulated pulse light emitted by the xenon lamp of the light source 14 used in the embodiments shown in FIGS. 1 and 2. From FIG. 3 it is understood that there is no remarkable variation in colors by the pulse number and that there is no large difference in colors between the DC lighting and the pulsed lighting. Hence, after the color correction factors Kr, Kg and Kb are once determined in the multipliers 16, 17 and 18, it is almost no need to change the color correction factors.

Figure 4:
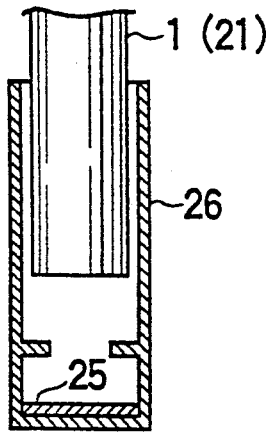
FIG. 4 is a cross sectional view of a tool for obtaining white balance correction factors to be used in the endoscope shown in FIGS. 1 and 2.

In FIG. 4, there is shown a tool 26 which is capable of fixing a comparative position between a scope 1 or 21 of an endoscope and a reference or standard white color plate 25. By using this tool 26, the white balance factors and the color correction factors may be calculated and set in the endoscope when the endoscope is forwarded from a factory in a market or the lamp of the light source is replaced with a new one. Of course, these factors may be calculated and set in the endoscope soon before the imaging.

Figure 5:
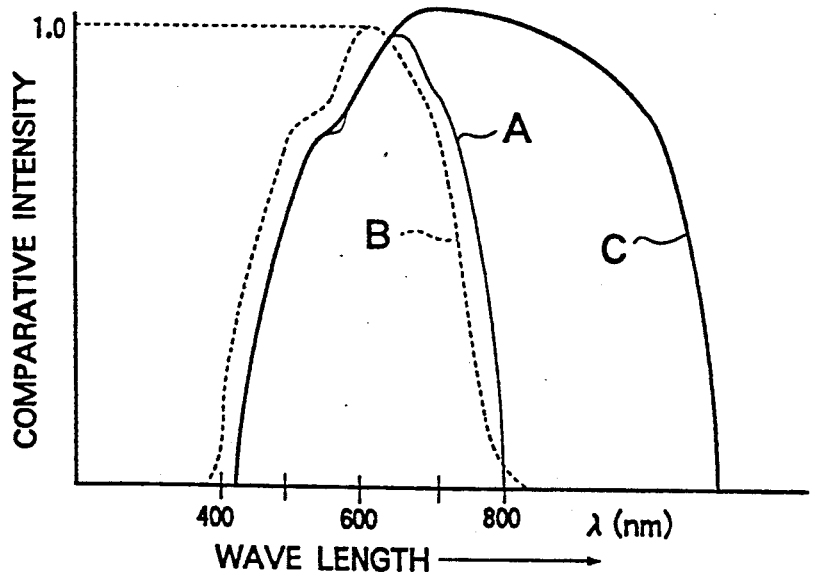
FIG. 5 is a graphical representation showing spectral characteristics of a continuous DC light and a pulsed light emitted by a light source unit used in the endoscope shown in FIGS. 1 or 2, and of a filter used in a third embodiment of an electronic endoscope according to the present invention.

In the third embodiment of an electronic endoscope according to the present invention, the color correction operation is carried out by using a low-band cut filter 30 having spectral characteristics such as a wave length property which is approximately the same as that of the continuous DC light in the lower half wave length band (see FIG. 5, line A), as shown by a line C in FIG. 5, in the still image pickup operation. That is, in the still image pickup operation, the low-band cut filter 30 is inserted in the light path in the light source unit portion, as shown in FIGS. 1 or 2, and the triple switch assembly 19 is controlled so as to pass the digital color image signals $R_1$, $G_1$ and $B_1$ to the respective image memories 9, 10 and 11, with the result of the same effects and advantages as those obtained in the first and second embodiments. In this embodiment, calculation of the color correction factors Kr, Kg and Kb is not required.

According to the present invention, the color correction operation may be also carried out between the image memories and the D/A converter or in the analog image signal processing.

Although the present invention has been described in its preferred embodiments with reference to the accompanying drawings, it is readily understood that the present invention is not restricted to the preferred embodiments and that various changes and modifications can be made by those skilled in the art without departing from the spirit and scope of the present invention.

What is claimed is:

1. An endoscope apparatus comprising:

an endoscope;

an endoscope body;

a light source for selectively emitting continuous light through the endoscope to the endoscope body during a moving-picture imaging operation or emitting pulsatory light during a still-picture imaging operation, the light spectral characteristic of said light source means being different from each other during said moving-picture imaging operation and said still-picture imaging operation;

imaging means for optically imaging through the endoscope a biological body under medical examination while illuminating said biological body by said light source means;

means for collecting said light, thereby to obtain electronic imaging signals thereof;

first multiplier means for multiplying said electronic imaging signals by a predetermined white balance coefficient so as to obtain white-balanced imaging signals; and second multiplier means for multiplying said white-balanced imaging signals with a predetermined color correcting coefficient during said still-picture imaging operation, thereby to obtain white-balanced still-picture color signals.

2. The endoscope of claim 1, also including a color separator for color-separating the color image signals picked up by the imaging means into color-separated color image signals for the primary colors.

3. The endoscope of claim 1, also including image memories for storing either white-balanced color image signals for the primary colors or color-corrected color image signals for the primary colors.

4. The endoscope of claim 1, also including a display for displaying either a color reproduction image on the basis of either the white-balanced color image signals or the color-corrected color image signals.

5. The endoscope of claim 1, wherein the means for collecting said light includes the imaging means and a camera control unit.

6. The endoscope of claim 1, wherein a tool fixes the comparative position between the scope and a reference white color plate in order to calculate the white balance coefficient and the color correcting coefficient.

7. An endoscope apparatus as claimed in claim 1, wherein said light source includes a xenon lamp.

8. An endoscope, comprising:
a scope having an image pickup device for picking up color image signals of an object to be observed;
a light source unit for outputting to the scope either a continuous DC light in a moving image pickup operation or a pulsed light in a still image pickup operation for illuminating the object;
means for obtaining white balance factors for primary colors;
means for carrying out a white balance operation of the color image signals by multiplying the image signals by the white balance factors; and
filter means having approximately the same wave length as that of the continuous DC light in its lower half wave length band, for carrying out a color correction operation of the color image signals in the still image pickup operation, the filter means being inserted in the path of the pulsed light emitted by the light source unit in the still image pickup operation.

9. The endoscope of claim 8, wherein the means for obtaining the white balance factors is a camera circuit.

10. The endoscope of claim 9, wherein the camera circuit includes the image pickup device and a camera control unit.

11. The endoscope of claim 8, wherein the means for carrying out a white balance operation includes a multiplier.

12. The endoscope of claim 8, also including a color separator for color-separating the color image signals picked up by the image pickup device into color-separated color image signals for the primary colors.

13. The endoscope of claim 8, also including image memories for storing either white-balanced color image signals for the primary colors or color-corrected color image signals for the primary colors.

14. The endoscope of claim 13, also including a display for displaying either a color reproduction image on the basis of either the white-balanced color image signals or the color-corrected color image signals.

15. The endoscope of claim 8, wherein a tool fixes a comparative position between the scope and a reference white color plate.

16. An endoscope apparatus comprising:
an endoscope;
an endoscope body;
a light source for selectively emitting light through the endoscope body during a moving-picture image operation or emitting pulsatory light during a still-picture imaging operation, the light spectral characteristic of said light sources means being different from each other during said moving-picture imaging operation and said still-picture imaging operation;
imaging means for optically imaging through the endoscope a biological body under medical examination while illuminating said biological body by said light source means;
means for converting the optical images to electronic imaging signals;
a white balance correction circuit including three multipliers and a triple switch assembly for selectively applying said electronic imaging signals to each multiplier, each multiplier multiplying said received electronic imaging signals by a predetermined white balance coefficient so as to obtain white balanced imaging signals; and
a color correcting means for multiplying said white-balanced imaging signals by a predetermined color correcting coefficient during said still-picture imaging operation, thereby to obtain white-balanced, still-picture color signals.

17. The endoscope apparatus of claim 16 in which the white balance operation is performed by a camera circuit.

* * * * *